United States Patent [19]

Sato et al.

[11] Patent Number: 5,714,643
[45] Date of Patent: Feb. 3, 1998

[54] PROCESSES FOR THE PREPARATION OF D-CHIRO-INOSITOL

[75] Inventors: Kiyoshi Sato, Hatano; Makoto Yoshida, Kamakura; Kenji Kanbe, Yokohama; Kiyoshi Hirazawa, Atsugi; Tomio Takeuchi, Tokyo, all of Japan

[73] Assignees: Hokko Chemical Co., Ltd.; Zaidan Hojin Biseibutsu Kagaku Kenkyu Kai, both of Tokyo, Japan

[21] Appl. No.: 596,131

[22] PCT Filed: Aug. 8, 1994

[86] PCT No.: PCT/JP94/01304

§ 371 Date: Feb. 9, 1996

§ 102(e) Date: Feb. 9, 1996

[87] PCT Pub. No.: WO95/04711

PCT Pub. Date: Feb. 16, 1995

[30] Foreign Application Priority Data

Aug. 11, 1993 [JP] Japan .................. 5-217926
Oct. 26, 1993 [JP] Japan .................. 5-288827
Jul. 4, 1994 [JP] Japan .................. 6-152181

[51] Int. Cl.$^6$ ................ C07C 35/14; C07C 35/16
[52] U.S. Cl. ................................................. 568/833
[58] Field of Search ............................... 568/833

[56] References Cited

U.S. PATENT DOCUMENTS

5,091,596  2/1992  Kennington et al. .............. 568/833

Primary Examiner—John Kight
Assistant Examiner—Everett White
Attorney, Agent, or Firm—Larson & Taylor

[57] ABSTRACT

An aqueous solution of kasugamycin or its salt is either mixed with a strongly acidic ion-exchange resin of the $H^+$-form in a reaction vessel, or is brought into contact with a strongly acidic ion-exchange resin of the $H^+$-form in a column containing said resin, followed by heating said aqueous solution and the resin under an atmospheric pressure or an elevated pressure, thereby to effect hydrolytic reaction of kasugamycin. By this reaction, an acidic reaction solution containing D-chiro-inositol is produced. This acidic reaction solution containing D-chiro-inositol is separated from the strongly acidic ion-exchange resin. Subsequently, D-chiro-inositol is recovered from the reaction solution. For this recovery, the acidic reaction solution is passed successively through a column of a strongly acidic ion-exchange resin of the $H^+$-form and through a column of a strongly basic ion exchange resin of the $OH^-$-form, so that a neutral aqueous eluate containing D-chiro-inositol is obtained. This neutral aqueous eluate is then concentrated and crystals of D-chiro-inositol are made to deposit, whereby D-chiro-inositol of a high purity can be harvested with high efficiency.

4 Claims, 1 Drawing Sheet

FIG. 1

PROCESSES FOR THE PREPARATION OF D-CHIRO-INOSITOL

TECHNICAL FIELD

This invention relates to improved processes for the preparation of D-chiro-inositol (hereinafter sometime abbreviated simply as "DCI").

In recent years, DCI is receiving attention as a therapeutic drug or preventive drug for non-insulin-dependent diabetes mellitus.

BACKGROUND ART

As processes for the preparation of DCI, the following processes (1) to (4) are known to date:

(1) A process for obtaining DCI, which comprises isolating pinitol (namely, a monomethyl ether derivative of DCI) as contained in a plant such as *Bougainvilles spectabilis*, sugar pine or redwood, by extracting said plant with a suitable solvent and then demethylating pinitol with hydroiodic acid or the like to produce DCI.

(2) A process for obtaining DCI, which comprises using as a starting material 1-chloro-2,3-dihydroxycyclohexa-4,6-diene, and producing DCI therefrom through several reaction steps [J. Org. Chem., 58, 2331–2339 (1993)].

(3) A process for obtaining DCI, which comprises using a halogenobenzene as a starting material, and producing DCI therefrom via several reaction steps [J. Chem. Sec. Parkin Trans. 1, 741–743 (1993)].

(4) A process for obtaining DCI, which comprises using as a raw material kasugamycin of high purity, heating it in 2N aqueous trifluoroacetic acid or 5N aqueous hydrochloric acid to hydrolyze kasugamycin and produce DCI, passing the resulting reaction solution, for the purpose of neutralization and elimination of impurities, through a column containing a strongly basic ion-exchange resin and a column containing a strongly acidic ion-exchange resin, and then crystallizing DCI from the liquid effluent as finally flown out of said resin column, by addition of ethanol to said effluent [see U.S. Pat. No. 5,091,596 specification (1992)].

Although a variety of the above-mentioned processes have been proposed as processes for the preparation of DCI as described above, they are accompanied by various drawbacks which do not allow advantageous preparation of DCI to be achieved on a commercial scale.

Thus, the process for the preparation of DCI according to said process (1), which includes the step of extracting pinitol from the plant, is cumbersome in making the extraction of pinitol and the purification of DCI formed, and can give only a low yield of DCI.

On the other hand, the process for the preparation of DCI according to said process (2) or (3), which includes the chemical synthesis steps, requires a stereospecific synthesis so that the reaction efficiency is low and the production cost of DCI is high.

The process (4) must use a very strong acid (aqueous solution of 5N hydrochloric acid or 2N trifluoroacetic acid, etc.) for the hydrolytic reaction of kasugamycin. Due to this very strong acid, side reactions can take place upon cleavage of kasugamycin molecules, and hence useless by-products are formed, resulting in a reduced yield of DCI. Further, this process requires such steps for the recovery and purification of DCI, where the strongly basic ion-exchange is used in a large quantity to neutralize the strong acid employed for the hydrolysis and also, the strongly acidic ion-exchange resin is also employed in a significant quantity to get rid of the basic compounds which have been formed as by-products, so that a further reduction can be involved in the yield of DCI. Besides, said process takes long time for operating the respective steps. In addition, a great deal of water is needed for the recovery of DCI and also for the regeneration etc., of the ion-exchange resins which were used in the purification of DCI. As a consequence, post-treatment of a large amount of waste water so formed is also needed. The process (4) therefore involves many problems.

There is hence an outstanding desire for the development of an industrially advantageous process for the preparation of DCI which can substitute for the above known preparation processes. In the above-mentioned circumstances, an object of this invention is to provide such a process which permits DCI to be produced at a high purity and high yield by simple and facile procedures.

DISCLOSURE OF THE INVENTION

We, the present inventors, have proceeded with an extensive investigation to solve the above problems. As a result, we have now devised such processes which can prepare DCI with commercial and many advantages by using kasugamycin as a raw material. Specifically, the present inventors have found that DCI can be produced with good reaction efficiency when hydrolysis of kasugamycin or its salt (unless otherwise specifically indicated, kasugamycin and its salt may hereinafter be collectively called "kasugamycin") is effected in such a manner that an aqueous solution of kasugamycin is mixed with a strongly acidic ion-exchange resin of the $H^+$-form in a batchwise operable reaction vessel and kasugamycin is hydrolyzed by heating said aqueous solution and the resin, and we have also found that when an acidic reaction solution containing DCI thus formed is then afforded from the hydrolysis of kasugamycin, DCI can be recovered subsequently from said reaction solution by applying thereto such a method which may have commonly been employed for the recovery of neutral saccharides.

Accordingly, in a first aspect of the present invention, there is provided a process for the preparation of D-chiro-inositol, characterized in that the process comprises mixing an aqueous solution of kasugamycin or a salt thereof with particles of a strongly acidic ion-exchange resin of the $H^+$-form, heating the resulting mixture under an atmospheric pressure or an elevated pressure to effect hydrolysis of kasugamycin, and after completion of the reaction, separating the resulting acidic reaction solution containing D-chiro-inositol so formed, from the strongly acidic ion-exchange resin, thereby to obtain the acidic reaction solution containing D-chiro-inositol, and then recovering D-chiro-inositol from said acidic reaction solution.

Further, the present inventors have also found that DCI can be efficiently produced when an aqueous solution of kasugamycin is continuously passed into and through a column containing a strongly acidic ion-exchange resin of the $H^+$-form while the aqueous solution of the kasugamycin present in the column is heated under an atmospheric pressure or an elevated pressure to hydrolyze the kasugamycin, and that an acidic reaction solution containing DCI thus formed is then afforded from the hydrolysis of kasugamycin, and DCI can be recovered from said reaction solution by applying thereto such a method which is commonly employed for recovery of neutral saccharides.

In a second aspect of the present invention, therefore, there is provided a process for the preparation of D-chiroinositol, characterized in that the process comprises continuously introducing an aqueous solution of kasugamycin or a salt thereof into a column as packed with a strongly acidic ion-exchange resin of the H$^+$-form, heating the aqueous solution of kasugamycin and the resin within said column under an atmospheric pressure or an elevated pressure to effect hydrolysis of kasugamycin, allowing the resulting acidic reaction solution containing D-chiro-inositol so formed, to flow out of the resin column, and recovering D-chiro-inositol from said acidic reaction solution.

Furthermore, it has also been found by the present inventors that, when, as in the above-described first aspect of the present invention, a strongly acidic ion-exchange resin of the H$^+$-form and an aqueous solution of kasugamycin are mixed together and reacted with each other under heating conditions to hydrolyze the kasugamycin and produce DCI with affording a reaction solution containing the DCI so formed, DCI crystals of a high purity can be efficiently obtained by conducting, for the purpose of recovering DCI from said reaction solution, the respective steps of passing said reaction solution through a column of a strongly acidic ion-exchange resin, then passing the acidic aqueous effluent as flown from said column, next through a column of a strongly basic ion-exchange resin, thereby to obtain a neutral aqueous eluate containing DCI, and then crystallizing DCI from the resulting neutral eluate. Thus, we have achieved a third aspect of the present invention.

Therefore, in the third aspect of the present invention, there is provided a process for the preparation of D-chiro-inositol, characterized in that the process comprises conducting successively the following first to fourth steps:

a first step, namely the step of mixing an aqueous solution of kasugamycin or a salt thereof with particles of a strongly acidic ion-exchange resin of the H$^+$-form, heating the resulting mixture under an atmospheric pressure or an elevated pressure to effect hydrolysis of kasugamycin, and after completion of the reaction, separating the resulting acidic reaction solution containing D-chiro-inositol so formed, from the strongly acidic ion-exchange resin, thereby to obtain the acidic reaction solution containing D-chiro-inositol, a second step, namely the step of passing said acidic reaction solution so obtained in the first step, through a column as packed with a strongly acidic ion-exchange resin of the H$^+$-form, to eliminate the basic impurities contained in said reaction solution and, if any unreacted kasugamycin is still remaining therein, also to eliminate the unreacted kasugamycin from said reaction solution, whereby an acidic aqueous solution containing D-chiro-inositol is obtained, a third step, namely the step of passing said acidic aqueous solution so obtained in the second step, through a column as packed with a strongly basic ion-exchange resin of the OH$^-$-form, thereby to obtain a neutralized aqueous eluate containing D-chiro-inositol, and a fourth step, namely the step of concentrating said eluate so obtained in the third step, and making D-chiro-inositol crystals of a high purity to deposit from the resulting concentrated solution.

Moreover, it has also been found by the present inventors that, when, as in the above-described second aspect of the present invention, an aqueous solution of kasugamycin is introduced in a column containing a strongly acidic ion-exchange resin of the H$^+$-form, and kasugamycin is then hydrolyzed with heating the aqueous solution in said column to produce DCI, and also to afford the reaction solution containing DCI which is flowed out of said column, DCI crystals of a high purity can be efficiently obtained by conducting, for the purpose of recovering the DCI from the DCI-containing reaction solution, the respective steps of passing said reaction solution through a column of a strongly acidic ion-exchange resin, then passing an acidic aqueous effluent as flown from said column, next through a column of a strongly basic ion-exchange resin, thereby to obtain a neutral aqueous eluate containing DCI, and then crystallizing DCI from the resulting neutral eluate.

In a fourth aspect of the present invention, therefore, there is provided a process for the preparation of D-chiro-inositol, characterized in that the process comprises conducting the following first to fourth steps:

a first step, namely the step of continuously introducing an aqueous solution of kasugamycin or a salt thereof into a column as packed with a strongly acidic ion-exchange resin of the H$^+$-form, heating under an atmospheric pressure or an elevated pressure the aqueous solution of kasugamycin and the resin within the column to effect hydrolysis of the kasugamycin, and allowing the resulting acidic reaction solution containing D-chiro-inositol so formed, to flow out of the resin column, thereby to obtain the acidic reaction solution containing D-chiro-inositol, a second step, namely the step of passing the acidic reaction solution so obtained in the first step, through a column as packed with a strongly acidic ion-exchange resin of the H$^+$-form to eliminate the basic impurities contained in said reaction solution and, if any unreacted kasugamycin is still remaining therein, also to eliminate the unreacted kasugamycin from said reaction solution, whereby an acidic aqueous solution containing D-chiro-inositol is obtained, a third step, namely the step of passing said acidic aqueous solution so obtained in the second step, through a column as packed with a strongly basic ion-exchange resin of the OH$^-$-form, thereby to obtain a neutralized aqueous eluate containing D-chiro-inositol, and a fourth step, namely the step of concentrating said eluate so obtained in the third step, and making D-chiro-inositol crystals of a high purity to deposit from the resulting concentrated solution.

The aqueous solution of kasugamycin or a salt thereof (for example, the hydrochloride or sulfate) which is used as a starting material in the process according to each of the first to fourth aspects of the present invention may be prepared and used generally, as will be described next. Thus, a kasugamycin-producing microorganism which has been modified to enhance its kasugamycin-producing capability is cultured in a usual manner, and from the resulting culture is isolated kasugamycin or its hydrochloride or sulfate according to a usual recovery method.

To ensure that kasugamycin or its hydrochloride or sulfate so recovered is used as a highly purified product, it is preferred to use such kasugamycin product which had been treated by some purification steps in advance. When a highly pure kasugamycin hydrochloride or sulfate is to be used, for example, such a powdery bulk product of kasugamycin hydrochloride or sulfate, which had been produced in Japan or abroad as a commercial-grade product of kasugamycin for use in the production of agricultural pesticides for controlling plant diseases, may be employed immediately by dissolving the kasugamicin product in deionized water etc., as long as it is of a high purity. Where the purity of the available kasugamycin product is low, however, this poorly pure kasugamycin product is better to be subjected to a preliminary purification by dissolving said product in deionized water etc. and then passing the resultant aqueous solution once through a column of activated carbon before it is used as the starting material.

BEST MODE FOR CARRYING OUT THE INVENTION

The processes according to the first to fourth aspects of the present invention will now be described in outline.

(I) Process according to the first aspect of the present invention

In the process according to the first aspect of the present invention, there may be used a tank-shaped or column-shaped reaction vessel which is operable batchwise. An aqueous solution of kasugamycin and particles of a strongly acidic ion-exchange resin ($H^+$-form) are mixed together in the reaction vessel. When the resultant mixture is then heated in the presence of said resin under an atmospheric pressure or an elevated pressure, the kasugamycin can be hydrolyzed so that DCI is produced. During the reaction, the reaction mixture may be either stirred or kept still without stirring.

As the strongly acidic ion-exchange resin ($H^+$-form) used in the first aspect of the present invention, an ion-exchange resin having sulfonic acid functions is preferred. Examples of such ion-exchange resin include such strongly acidic ion-exchange resins available in the market, for example, "Diaion"® SK116, "Diaion"® PK228, "Amberlite"® IR120B, "Amberlite"® 200C, "Amberlite"® 201B, "Duolite"® C-20, "Duolite"® C-264, and "Duolite"® XE-636. "Diaion", "Amberlite" and "Duolite" all are the registered trademarks.

The concentration of kasugamycin in the aqueous solution of kasugamycin used may be 0.1–30% by weight, and may preferably be 10–25% by weight. When there is used such an aqueous solution of kasugamycin which has a high kasugamycin concentration as much as possible-(amounting to 10–25% by weight) and which may be prepared by dissolving kasugamycin in water, if necessary, with heating the water to about 60° to 80° C., it is then feasible to carry out in a facile way the procedures for the recovery and purification of DCI (particularly, the procedures for concentrating the aqueous solution of DCI produced), which are to be conducted after the step for the hydrolysis of kasugamycin was effected. It is preferable to employ the strongly acidic ion-exchange resin ($H^+$-form) in such an amount that the resin as employed can provide at least an ion-exchanging capacity as much as one-fold or higher than the ion-exchanging capacity which is equivalent to the molar equivalent quantity of kasugamycin present.

In such a mode of the reaction procedure that the hydrolytic reaction of kasugamycin is conducted in the batchwise operable reaction vessel, the degree of hydrolysis of kasugamycin can be enhanced much higher, when the reaction temperature is elevated much higher (for instance, in case when the reaction is conducted under an atmospheric pressure, there may be employed a reaction temperature which is close to the boiling point of water), and also when the reaction time is increased much longer. The yield of DCI can be improved much more when the degree of hydrolysis of kasugamycin is enhanced much higher. However, it is necessary to operate the strongly acidic ion-exchange resin at a temperature lower than such a maximum temperature at which the resin employed can retain its durability (for instance, the resin of "Diaion"® SK116 can retain its durability at a temperature of 120° C. but the resin of "Duolite"® CC-204F can retain its durability at a temperature of 135° C. at maximum), in order to enable the strongly acidic ion-exchange resin to be used repeatedly for the hydrolysis of kasugamycin by making regeneration of the resin once exhausted. The reaction temperature and reaction time for the hydrolysis of kasugamycin may vary depending on the kind of the strongly acidic ion-exchange resin employed. When "Diaion"® SK116 is used, for example, the reaction temperature may be 50°–100° C., preferably 90°–98° C. under an atmospheric pressure, and the reaction time may then be 6–60 hours, preferably 10–48 hours. When the reaction is conducted with stirring the reaction mixture under such conditions as above, kasugamycin can undergo the hydrolysis at a rate of the conversion of nearly 100% and be converted into DCI.

With using the strongly acidic ion-exchange resin ($H^+$-form) same as that described above, the hydrolysis of kasugamycin can also be conducted under an elevated pressure which is high sufficiently to prevent the boiling of water present in the reaction mixture. This procedure makes it possible to conduct the reaction in a shorter time. Thus, when the hydrolytic reaction is conducted, for example, under a pressure of 0.1–3 kg/cm$^2$ (gauge), preferably under a pressure of 0.5–1.2 kg/cm$^2$ (gauge) at a temperature of 110°–120° C., the hydrolytic reaction of kasugamycin may be completed, for example, in 1–12 hours, preferably in 1–6 hours and thus DCI can be produced in the resulting reaction solution at a yield of nearly 100% based on the theoretical yield. When the hydrolytic reaction of kasugamycin is conducted under such elevated pressure as described above, it is desirable to employ a reaction vessel having a pressure-resistant structure or to carry out the reaction with placing a reaction vessel in an autoclave. In this case, it is not essential to stir said reaction mixture.

After the completion of the hydrolytic reaction of kasugamycin, the whole mixture of the resin with the resulting acidic reaction solution as formed is cooled to a temperature lower than 50° C., preferably to room temperature, as needed. Said resulting acidic reaction solution can be separated by filtration from the strongly acidic ion-exchange resin. The acidity of said acidic reaction solution so obtained as the filtrate may vary depending on the amounts and kinds of kasugamycin and the strongly acidic ion-exchange resin employed and other factors, but generally said acidity may be equivalent to about 0.05–1.0N. Further, when the resin collected as the filtration residue is washed by adding thereto water in a volume 0.8–1 times that of the resin, the DCI remaining present in the resin can be eluted out in the water so that aqueous washings containing DCI are collected. The aqueous washings may be combined with the acidic reaction solution which was obtained as the aforesaid filtrate.

DCI can then be recovered from the acidic reaction solution by applying a conventional method Which is commonly employed for the recovery of neutral saccharides.

Upon conducting the step of hydrolyzing kasugamycin by the process according to the first aspect of the present invention, the hydrolyric reaction can be operated batchwise also by employing a column-shaped reaction vessel instead of the tank-shaped one. When a column-shaped reaction vessel is employed and when the subsequent different steps for the recovery of DCI from the reaction solution as obtained in the hydrolysis step are then conducted with using the different resin columns, it is feasible to conduct the individual steps of the process in a series of devices which are successively or continuously connected with each other to carry out the aforesaid steps, whereby the reaction solution can be made unnecessary to be discharged out of a system consisting of the connected devices employed, and thus the preparation of DCI of a high purity can be achieved with good operability.

The size of a column-shaped reaction vessel to be employed for said hydrolytic reaction can suitably be changed depending on the concentration and amount of the aqueous solution of kasugamycin to be used. When practicing at a small scale, a column-shaped reaction vessel having an inner diameter of about 5–6 cm and a height of approximately 4–10 cm may be used. A column-shaped reaction vessel having a larger inner diameter can also be used, in order to make it possible to mix the aqueous solution of kasugamycin with the resin under stirring.

(II) Process according to the second aspect of the present invention

In the process according to the second aspect of the present invention, an aqueous solution of kasugamycin is continuously introduced into a column containing therein a strongly acidic ion-exchange resin ($H^+$-form). And, the aqueous solution of kasugamycin and the resin within said column are heated to a predetermined reaction temperature under an atmospheric pressure or elevated pressure, to effect the hydrolysis of kasugamycin, while the aqueous solution is passed through the resin column. The aqueous solution which flows through the resin column is controlled to be passed through said resin column at such a rate that said aqueous solution is allowed to reside in the resin column for a retention time which will be required for the hydrolytic reaction of kasugamycin to be completed in the resin column. Then, the aqueous solution is allowed to flow out of the resin column. In this manner, the acidic reaction solution containing DCI as produced by the hydrolysis of kasugamycin is afforded with being allowed to flow out of said resin column of the strongly acidic ion-exchange resin. The step of recovering the DCI from said acidic reaction solution is subsequently conducted.

In the above-mentioned mode of the reaction procedure that the hydrolysis of kasugamycin is conducted within the resin column according to the process of the second aspect of the present invention, a commercially available, strongly acidic ion-exchange resin, which is same as that used in the aforesaid mode of the batchwise reaction procedure according to the first aspect of the present invention, may be used and is first prepared in its $H^+$-form and then packed in a column. An aqueous solution of kasugamycin is then passed through the resin column which has been so prepared as above and heated to a predetermined reaction temperature, and in this way the intended hydrolysis of kasugamycin can be performed. The degree of hydrolysis of kasugamycin can be increased much higher when the reaction temperature is elevated much higher, when the retention time of the aqueous kasugamycin solution passing through the column is increased much longer, and when the amount of the resin is increased much greater.

The efficiency of the hydrolyric reaction can vary somewhat depending on the kind of the resin employed. When "Diaion"® SK116 ($H^+$-form) is employed as an example of the strongly acidic ion-exchange resin, kasugamycin can be hydrolyzed at a degree of the hydrolysis of nearly 100%, by maintaining the temperature inside the resin column at 90°–98° C. and by adjusting the flow rate of the solution passing through the resin column so that the retention time of the solution passing through the column is at least 6 hours. In general, the temperature inside the column of the strongly acidic ion-exchange resin may be maintained at a temperature of 60°–98° C., preferably at a temperature of 90°–98° C. under an atmospheric pressure or may be maintained at 100°–150° C. under an elevated pressure condition. Thus, at these elevated temperatures, the hydrolysis of kasugamycin can well be carried out. At these elevated temperatures, the hydrolytic reaction of kasugamycin can be conducted well efficiently when the retention time of the solution passing through the column is controlled to be 6–40 hours, preferably 7–15 hours.

Further, the hydrolytic reaction of kasugamycin may be carried out at a temperature of 100°–150° C. under an elevated pressure which is high sufficiently to prevent the boiling of water in the resin column, for example, under a pressure of 0.1–3 $kg/cm^2$, preferably at a pressure of 0.5–1.2 $kg/cm^2$ (in terms of the gauge pressure), while the retention time of the solution passing through the resin column is controlled to be 1.0–10 hours, preferably 3–5 hours.

When the hydrolytic reaction of kasugamycin is conducted under elevated pressures, it is desirable to give a pressure-resistant structure to such a vessel in which the column of the strongly acidic ion-exchange resin is placed, and also to pump under pressure the feeded aqueous solution of kasugamycin into the resin column.

In the mode of the reaction procedure that the hydrolysis of kasugamycin is conducted within the resin column, it is possible to enhance the degree of the hydrolytic reaction by repeating the reaction in a single resin column, namely by recirculating and introducing the acidic reaction solution which has once flown from the column of the strongly acidic ion-exchange resin, again into an inlet of the same resin column so that the reaction solution is passed repeatedly through the resin column.

There is a further mode of the reaction procedure which may be deemed as a modification of the aforesaid batchwise reaction procedure. In this further mode, the aqueous solution of kasugamycin is subjected to the reaction for a predetermined time by temporarily holding the aqueous solution to remain within the resin column of a strongly acidic ion-exchange resin with closing the outlet of the resin column. After checking the concentration of DCI as formed in said aqueous solution held in the resin column, the reaction solution containing DCI may then be allowed to flow from opened outlet of said column by pumping a volume of deionized water, etc., into the inlet of said column.

Whichever mode of the reaction procedure is employed, the operation of the process can proceed without discharging the reaction solution from the device system during the reaction conducted, and the acidic reaction solution just flown from the resin column can then be fed to the next step of the process, as the very reaction solution where the hydrolytic reaction of kasugamycin has completed.

It is then necessary and possible to recover DCI from the resulting reaction solution containing DCI, by applying thereto a conventional method which is commonly employed for recovery of neutral saccharides.

(III) Process according to the third aspect of the present invention

Briefly speaking, the process according to the third aspect of the present invention comprises four steps, namely the first to fourth steps. Methods for practicing each of these four steps are now described in more details.

(1) Method for practicing the first step

The first step has various sub-steps wherein an aqueous solution of kasugamycin is mixed with a strongly acidic ion-exchange resin in a reaction vessel which is operable in a batchwise manner, the hydrolysis of kasugamycin is conducted in said vessel, and thus the resulting acidic reaction solution containing DCI therein is afforded. This first step can be conducted in a manner same as that described above with respect to the process of the first aspect of the present invention.

(2) Method for practicing the second step

In the second step of the process according to the third aspect of the present invention, the acidic reaction solution containing DCI as obtained in the above first step is passed through a column containing a strongly acidic ion-exchange resin for the purpose of purification of DCI. This step makes it possible to eliminate the unreacted remaining kasugamycin, as well as any basic substances which are by-produced in the first step, from said acidic reaction solution.

As the strongly acidic ion-exchange resin employed here, there may be employed such a resin same as that used in the first step, for example, a resin available under a registered trade mark "Diaion"® SK116, which may be first prepared in its $H^+$-form and then packed in a column. At this time, the amount of the resin which may be packed in the column may vary depending on the amounts of the basic components which are contained in the acidic reaction solution as obtained in the first step but are to be eliminated. In a usual case, however, the strongly acidic ion-exchange resin may be used in such an amount which is substantially same as the amount of the resin employed in the first step.

The acidic reaction solution, which has been obtained by passing through the column in this second step, can then be fed directly to the next step, i.e., the third step. For effecting the elution of the DCI which is remaining in the strongly acidic ion-exchange resin employed in the second step, it is possible to wash said resin by charging a same volume of deionized water as that of the resin into a top of the resin column. The resultant aqueous washing may then be combined with the above-mentioned acidic reaction solution. When the thus-combined liquid mixture is fed to the third step, it is possible to recover DCI at a still improved yield.

(3) Method for practicing the third step

The third step of the process according to the third aspect of the present invention is conducted in order to neutralize such acids which have been formed by the hydrolytic reaction etc., and are present in the acidic aqueous solution as obtained from said second step. As a method for the neutralization of the acids, said DCI-containing acidic aqueous solution as obtained from the second step is passed through a column containing a strongly basic ion-exchange resin, whereby a neutral aqueous eluate containing DCI is obtained from the latter resin column.

Examples of the strongly basic ion-exchange resin of the $OH^-$-form, which is employed in the third step, include ion-exchange resins containing quaternary ammonium groups as functional groups, such as the resins available under registered trademarks "Duolite"® A-113PLUS and "Amberlite"® IRA 410. The amount of the basic ion-exchange resin which is to be packed in the column may vary depending on the amount of the acidic components which are present in the reaction solution as treated in the second step and are to be eliminated in the third step. In general, however, when the strongly basic ion-exchange resin is employed in such an amount which is ranging from the amount same as the amount of the resin employed in the first step, but to an amount of two-folds much than the amount of the resin employed in the first step, the basic ion-exchange resin as employed can adsorb the acidic components which are present in the aqueous DCI solution, with neutralizing this aqueous DCI solution.

The aqueous DCI solution, which has been neutralized and obtained from this third step as the eluate from the resin column, may be fed directly to the next step, namely, the fourth step. DCI can however be recovered at an improved yield if the resin as employed in the third step is washed, like in the second step, with a volume of deionized water and the resultant aqueous washing is combined with said aqueous DCI solution before being fed to the fourth step. If it is desired to further purify the DCI-containing eluate which has been neutralized by the third step, said eluate may be passed through a column containing an adsorbent such as activated carbon.

By conducting the second and third steps of the process according to the third aspect of the present invention, it is feasible to eliminate entirely the impurities which were present in the kasugamycin employed as the starting material, and the by-products which are formed from the impurities through the hydrolytic reaction in the first step of the process, as well as the by-products which are formed by the hydrolysis of kasugamycin. As a consequence, an aqueous solution containing DCI at a high purity can be afforded.

(4) Method for practicing the fourth step

In the fourth step of the process according to the third aspect of the present invention, DCI is recovered from the neutral aqueous eluate which has been obtained in the above third step and which contains DCI and is practically free from impurities. For the recovery of DCI, it is only necessary to concentrate said eluate and then to crystallize DCI. For example, said eluate may be concentrated by heating under reduced pressure in a rotary evaporator. The concentrated solution so obtained may be heated to 60°–80° C. or so. To the concentrated solution so heated is added under stirring ethanol which has also been heated to the same temperature. When the temperature of the resultant mixture is then allowed to cool down to room temperature, DCI gradually crystallizes. Subsequent to the deposit of crystals, the crystals may be collected by filtering through a glass filter and then dried, whereby DCI, the target substance, is obtained as colorless crystals. In this case, colorless crystals of DCI can be obtained in a short time when the crystals are dried under reduced pressure at 50°–120° C., preferably 90°–110° C. for 2–5 hours. Generally, the recovery of DCI is possible also by applying a conventional method commonly employed for depositing crystals of a saccharide from a thick solution of the saccharide, for example, such a method wherein a thick aqueous solution of the saccharide is left still in cold to deposit the crystals.

When these first to fourth steps are conducted successively according to the third aspect of the present invention, there can be obtained DCI which has been purified to substantially 100% purity.

The process according to the third aspect of the present invention will be illustrated in Examples 1–11 and 15–16 hereinafter.

(IV) Process according to the fourth aspect of the present invention

The process according to the fourth aspect of the present invention comprises the following four steps. Each of these steps can be practised as will be described below.

(1) Method for practising the first step

This first step comprises the sub-steps wherein an aqueous solution of kasugamycin is continuously introduced into a column containing a strongly acidic ion-exchange resin packed therein, and wherein the hydrolysis of the kasugamycin is effected with passing the aqueous solution through the resin column and with keeping said aqueous solution to reside in the resin column for a retention time, so that an acidic reaction solution containing DCI is obtained as the effluent from said column. This first step may be conducted in a manner same as that described above with respect to the process of the second aspect of the present invention.

(2) Method for practising the second step

This second step is conducted to eliminate the basic substances from the acidic reaction solution as obtained in the first step. This second step may be practised in a manner same as the second step of the process according to the third aspect of the present invention.

(3) Method for practising the third step

This third step is conducted to eliminate the acidic components from the aqueous DCI solution as obtained in the second step, so that the aqueous DCI solution is neutralized. This third step may be practised in a manner same as the third step of the process according to the third aspect of the present invention.

(4) Method for practising the fourth step

This fourth step is conducted to crystallize DCI from the neutral aqueous DCI solution as obtained in the third step. This fourth step may be practised in a manner same as the fourth step of the process according to the third aspect of the present invention.

These first to third steps of the process according to the fourth aspect invention may be carried out individually and independently at different times. While, some or all of the first to third steps of the present process may also be conducted in a continuous manner by connecting several or all of the resin columns, which each are used in these steps, with each other by means of conduits, and by adjusting the flow rates of the solutions passing through the respective resin columns so connected, by means of controllable pumps which are interposed in said conduits.

In the above case, the volume of one solution which can pass through one resin column to be treated by the possage through this resin column in the second and/or third steps can be governed by the rate of passage of the solution through the resin column used in the first step where the hydrolytic reaction is effected. In order to increase the kasugamycin-hydrolyzing velocity in the first step, it will be an effective means to establish a condition of elevated pressure within the resin column used for the first step and to heat the solution under the reaction to 100° C. or higher in said resin column. Further, the resins each employed in the first to third steps can be regenerated by acid or alkali treatment. Hence, these resins may be re-utilized and used repeatedly and semi-permanently if the resins which have once been packed in the columns are subjected to the regenerating treatments in situ in the resin columns.

Figure 1:
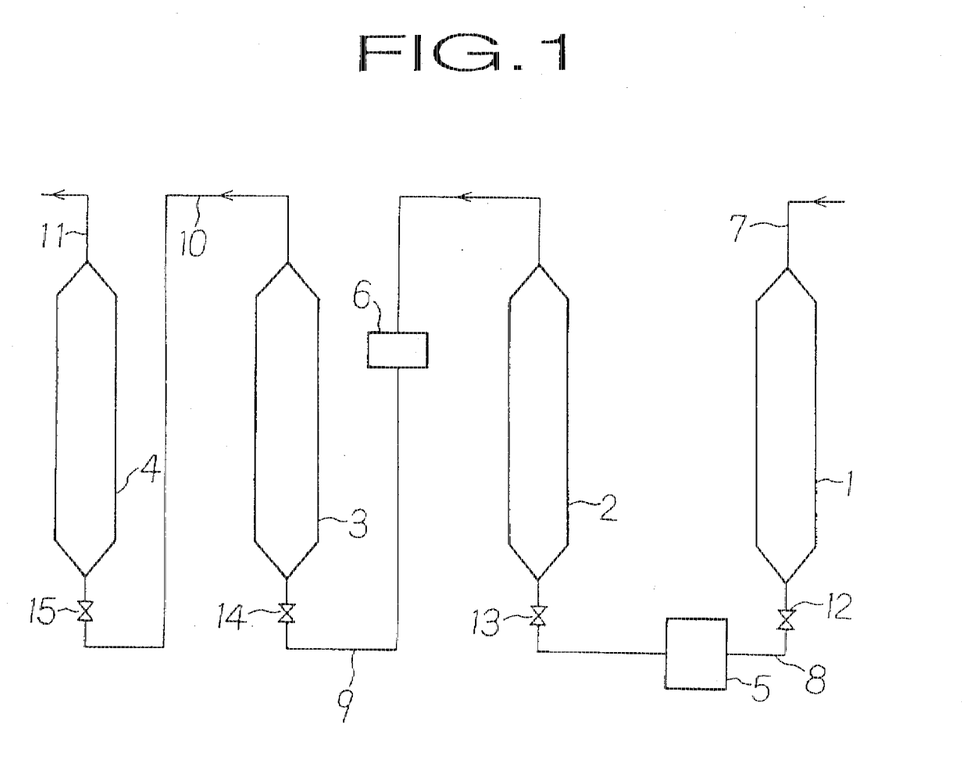
FIG. 1 of the accompanying drawing shows diagrammatically the device which is suitable for conducting the process according to the fourth aspect of the present invention.

Now, a device which is suitable for conducting in a continuous manner the first step to the third step of the process of the fourth aspect of the present invention is diagrammatically depicted in brief in FIG. 1 of the accompanying drawing.

This device comprises a column 1 as packed with activated carbon, a column 2 as packed with a strongly acidic ion-exchange resin ($H^+$-form) which works as a hydrolyzing reactor of a columnar shape, a purifying column 3 as packed with a strongly acidic ion-exchange resin ($H^+$-form), and a purifying column 4 as packed with a strongly basic ion-exchange resin ($OH^-$-form). The activated carbon column 1 has an inlet in the top portion thereof and is provided at said inlet with a feed conduit 7 for an aqueous solution of a crude kasugamycin (or its salt) to be used as the starting material. An outlet in the bottom portion of the column 1 is connected through a conduit 8 to the strongly acidic ion-exchange resin column 2 for effecting the hydrolytic reaction of kasugamycin. In this conduit 8, an on-off valve 12 and another on-off valve 13 are interposed on a side of the outlet of the column 1 and on a side of the inlet of the column 2, respectively. Further, a liquid-feeding pump 5 is arranged at a position intermediate between the valve 12 and the valve 13. As the pump 5 is preferred a pump of the flow rate-controllable type such that the flow rate of the liquid stream passing through the conduit 8 can optionally be increased or decreased.

An outlet of the strongly acidic ion-exchange resin column 2 (the hydrolyzing reactor) is connected with an inlet of the strongly acidic ion-exchange resin column 3 for the purification, by a conduit 9. In the conduit 9 is inserted a venting device (valve) 6 in order to release gas off, if the gas would be mixed in the reaction solution as flowed from the column 2. Further, an on-off valve 14 is also inserted in the conduit 9.

An outlet of the strongly acidic ion-exchange resin column 3 for the purification is connected with an inlet of the strongly basic ion-exchange resin column 4 for the purification, by a conduit 10 which is provided with an on-off valve 15. At an outlet of the column 4 is provided a conduit 11 for discharge of the solution flowing from the column 4. The discharge conduit 11 is further arranged to deliver the aqueous solution of D-chiro-inositol, which has flown from the column 4 and has been neutralized and purified, to a receptacle (not shown) for collecting said aqueous solution. A concentrating means (not shown) for concentrating the aqueous D-chiro-inositol solution as collected in said receptacle is placed downstream the column 4.

Besides, the strongly acidic ion-exchange resin column 2 working as the hydrolyzing reactor may be arranged in a suitable heating means which surrounds said column, such as heating jacket or oven, so that the resin within the column 2, as well as the solution flowing through said column and undergoing the reaction are heated to an elevated reaction temperature of 50° C. or higher.

The process according to the fourth aspect of the present invention will be illustrated in Examples 12–14 and 17 hereinafter.

BRIEF DESCRIPTION OF THE DRAWING

This device comprises the column 1 of activated carbon, the hydrolyzing reactor 2 composed of the column of the strongly acidic ion-exchange resin ($H^+$-form), the column 3 of the strongly acidic ion-exchange resin ($H^+$-form), the column 4 of the highly basic ion-exchange resin ($OH^-$-form), the liquid-feeding pump 5, the venting valve 6, the conduit 8, and the on-off valve 12.

The processes according to the present invention will next be illustrated specifically with reference to the following Examples to which the present invention is limited in no way.

EXAMPLE 1

This Example illustrates the process according to the third aspect of the present invention, which comprises the steps of preparing an aqueous solution of kasugamycin hydrochloride used as a starting material, mixing said aqueous solution with particles of a strongly acidic ion-exchange resin ($H^+$-form) in a reaction vessel and hydrolyzing kasugamycin under heating.

(1) First step (the hydrolyzing step)

Crystals of kasugamycin hydrochloride (15.5 g, with a purity of 97.1%) were weighed and placed in an eggplant-shaped flask of 500 ml-capacity, followed by addition of 100 ml of deionized water thereto so that the crystals were dissolved to give an aqueous solution of kasugamycin hydrochloride. With this aqueous solution were mixed 100 ml of "Diaion"® SK116 (H⁺-form) (a strongly acidic ion-exchange resin having an ion-exchanging capacity of 2.1 milli-equivalents per ml). The resulting mixture was heated under an atmospheric pressure at 95° C. for 12 hours under stirring by a magnetic stirrer, whereby hydrolysis of kasugamycin was effected.

The resultant reaction mixture was cooled down to room temperature, and the strongly acidic ion-exchange resin was filtered off therefrom. The acidic aqueous filtrate so obtained was the reaction solution containing DCI as formed. When a portion of this filtrate was titrated with an 0.1N solution of sodium hydroxide, it was found that said filtrate showed an acidity equivalent to a 0.7N aqueous acid. Further, the resin which had been filtered off was washed with 100 ml of deionized water, and the resulting washing liquids (the aqueous washings) were combined with said filtrate to afford 230 ml of the acidic reaction solution (which contained DCI at a yield equivalent to 98%).

Incidentally, a portion of the aforesaid acidic aqueous filtrate, namely, of the acidic reaction solution containing DCI as formed by the hydrolysis of kasugamycin was sampled and subjected to thin-layer chromatography (TLC) on silica gel layers (product of Merck & Co., Inc.; "Art 5715") (with developing solvent composed of n-butanol-acetic acid-water, 2:1:1 by volume), and the silica gel layers were then subjected to staining tests with ninhydrin, vanillin-sulfuric acid, potassium per-manganate and iodine vapor, respectively, for the comparison purpose. According to these staining tests, a spot of DCI (in the vicinity of Rf=0.39) was observed by the color development with each of potassium permanganate and vanillin-sulfuric acid, and in addition, spots of by-products (in the vicinity of Rf=0.58) were observed by the color development with ninhydrin, vanillin-sulfuric acid or iodine vapor. This indicates that the amounts of by-products as formed additionally to DCI through the hydrolytic reaction of kasugamycin were only minor.

(2) Second step (the step for elimination of basic substances)

The acidic reaction solution as obtained from the above first step was introduced into a top of a column (having an inner diameter of 2 cm and a height of 22 cm) which was packed with a strongly acidic ion-exchange resin ("Duolite"® C-20, H⁺-form, 70 ml), so that said reaction solution was then passed through the resin column, whereby an effluent was obtained from said column. After the reaction solution had been passed through the resin column, the resin column was washed with 70 ml of deionized water. The aqueous washing obtained was combined with the column effluent as obtained beforehand, whereby 300 ml of an acidic aqueous solution containing DCI were obtained.

(3) Third step (the neutralization step)

About 300 ml of the acidic aqueous solution as obtained in the second step were loaded into a top of a column (having an inner diameter of 2.4 cm and a height of 22 cm) which was packed with a strongly basic ion-exchange resin ("Duolite"® A-113PLUS", OH⁻-form, 100 ml), so that said acidic aqueous solution was then passed through the resin column. An aqueous eluate, which had flowed from the outlet of the resin column, was collected in fractions. Thus, the first 100ml fraction of the eluate were discarded and the next fractions of about 200 ml of the eluate were then collected. Further, the resin was washed with 100 ml of deionized water. About 100 ml of the aqueous washing were combined with the column eluate which was collected beforehand. In this way, about 300 ml of a neutral aqueous solution containing DCI were afforded.

The above neutral aqueous solution was a solution of DCI which had been neutralized and purified to a high purity. The content of DCI in this neutral aqueous solution of DCI was found to be 5.9 g (as compared to the theoretical value of 6.2 g)(the yield of DCI obtained was 94%, and a calculated purity of DCI was about 99%) when measured by a high performance liquid chromatography.

(4) Fourth step (the step for crystallization of DCI)

About 300 ml of the neutral aqueous solution as obtained in the third step were concentrated to a volume of about 25 ml by a rotary evaporator, followed by heating the concentrated solution to 70° C. The concentrated hot solution was added under stirring with 225 ml of ethanol which had been heated to 70° C. The resulting liquid mixture was left still standing at room temperature for about 12 hours, so that crystallization of DCI was effected. After crystals had deposited, the crystals were collected by filtration with a glass filter. The crystals were then dried under reduced pressure at 105° C. for 4 hours, whereby 5.8 g of colorless crystals of DCI were harvested (at a yield of 94% and purity of about 100%).

Analytical data and physical data of the colorless DCI crystals obtained are shown below.

Appearance: colorless crystals

Melting point: 238° C.

Specific rotation: $[\alpha]_D^{23}$ +65° (c 1.0, water)

Analysis by liquid chromatography:

A single peak of DCI was observed under the following conditions:

Analysis conditions:

Column: ZORBAX-NH$_2$ (4.6×250)

Detector: Shodex RI SE-51

Solvent: 80% MeCN-H$_2$O

Flow rate: 2.5 ml/min

From the foregoing, the above colorless crystals were confirmed to be pure D-chiro-inositol.

EXAMPLE 2

This Example illustrates the process according to the third aspect of the present invention, which comprises the steps of preparing and mixing an aqueous solution of kasugamycin used as a starting material with particles of a strongly acidic ion-exchange resin in a reaction vessel and hydrolyzing kasugamycin under an atmospheric pressure.

Similarly to the first step of Example 1, 100 ml of an aqueous solution of kasugamycin (in its free base form) (15 g, with a purity of 98%) were charged in an eggplant-shaped flask of 500 ml-capacity. A strongly acidic ion-exchange resin ("Diaion"® SK116, H⁺-form, 100 ml) was added to said aqueous solution. While stirring the resultant mixture, this mixture was heated under an atmospheric pressure at 95° C. for 12 hours, so that the hydrolysis of kasugamycin was effected.

The whole reaction mixture thus obtained was cooled to room temperature, and then the strongly acidic ion-exchange resin was filtered off therefrom to give the filtrate. The resin was then washed with 100 ml of deionized water. The filtrate and the aqueous washing were combined together so that about 230 ml of the acidic reaction solution containing DCI were obtained. This acidic reaction solution was treated similarly to the procedures of the second, third and fourth steps of Example 1, whereby 6.6 g of DCI of a high purity were harvested (at a yield of 94% and purity of 100%).

EXAMPLES 3–11

Each of these Examples illustrates the process according to the third aspect of the present invention, comprising the steps of using kasugamycin hydrochloride as a starting material and hydrolyzing kasugamycin.

Crystals of kasugamycin hydrochloride (10.0 g, with a purity of 99%) as furnished were dissolved in deionized water to give an aqueous solution of kasugamycin hydrochloride. This solution was then subjected to the hydrolysis step (the first step) similarly to Example 1. Various conditions of the reaction, including the kind and amount of the resin, the reaction temperature and the reaction time employed in the hydrolysis step were changed, as will be described in Table 1a to Table 1b given hereinafter.

The first step to the fourth step in each Example were conducted as described below: (1) First step (the hydrolysis step)

Crystals of kasugamycin hydrochloride (10.0 g) were weighed and placed in an Erlenmeyer flask of 500 ml-capacity, and were then dissolved in 50 ml of deionized water under heating to prepare an aqueous solution of kasugamicin hydrochloride. The strongly acidic ion-exchange resin (as prepared in its $H^+$-form) as indicated in Table 1a or Table 1b hereinafter was further added into the flask and mixed with said aqueous solution. Under an atmospheric pressure or under an elevated pressure while the flask being placed in an autoclave, the hydrolytic reaction of kasugamycin was then conducted in the batchwise manner. During the reaction, the reaction mixture was kept still without stirring. Thereafter, the whole reaction mixture was cooled to room temperature, and filtered to separate the strongly acidic ion-exchange resin and the filtrate. The resin was washed with 50 ml of deionized water. The aqueous washing and the filtrate were combined together to afford about 140 ml of the acidic reaction solution containing DCI.

(2) Second to fourth steps

After completion of the hydrolysis step, all the steps of recovering DCI from the reaction solution obtained in the first step, namely, the second to fourth steps, including the crystallization of DCI, were conducted in the following ways (a) to (c) similarly to Example 1.

(a) The column of a strongly acidic ion-exchange resin which was employed in the second step had been prepared by packing a column (2×16 cm) with 50 ml of "Duolite"® C-20 ($H^+$-form). DCI-containing fractions of the eluate as eluted from this resin column were combined with 50 ml of an aqueous washing which was obtained by washing said resin column with water, whereby about 175 ml of an acidic aqueous solution containing DCI were obtained.

(b) The column of a strongly basic ion-exchange resin which was employed in the third step had been prepared by packing a column (2×19 cm) with 60 ml of "Duolite"® A-113PLUS ($OH^-$-form). DCI-containing fractions of the eluate as eluted from this resin column were combined with 60 ml of an aqueous washing which was obtained by washing said resin column with water, whereby about 200 ml of a neutralized aqueous eluate containing DCI were obtained.

(c) In the fourth step, about 200 ml of the neutral aqueous eluate as obtained in the third step were concentrated to a volume of about 10 ml, and the concentrated solution was heated to about 70° C., followed by mixing with 70 ml of hot ethanol at 70° C. The resultant mixture was left still at room temperature for about 12 hours to allow crystals of DCI to deposit. The crystals so deposited were collected by filtration and then dried. The purity and yield of the DCI collected were checked. The results are summarized in Table 1a to Table 1b shown hereinafter.

EXAMPLE 12

This Example illustrates preparation of DCI according to the process of the fourth aspect of the present invention, which is conducted using an aqueous solution of a crude kasugamycin hydrochloride as a starting material.

A system of the reaction apparatus used to conduct this Example was constructed, as diagrammatically illustrated in FIG. 1 of the accompanying drawing, by connecting with each other by means of conduits a column of activated carbon for the preliminary purification of the crude kasugamycin, a column of a strongly acidic ion-exchange resin ($H^+$-form) as the kasugamycin-hydrolyzing reactor, a column of a strongly acidic ion-exchange resin ($H^+$-form) for the purification of the DCI-containing reaction solution, and a column of a strongly basic ion-exchange resin ($OH^-$-form) for the additional purification of the DCI solution.

(1) Preliminary purification step for crude kasugamycin

A crude powdery commercial product of kasugamycin hydrochloride (with a purity of 71%, 24 g) was dissolved in 120 ml of deionized water under heating. In this manner, an aqueous solution of the kasugamycin hydrochloride containing impurities was prepared. This entire aqueous solution was loaded on the top of a column (having an inner diameter of 1.5 cm and a height of 14 cm) as packed with 25 ml of activated carbon and was then forced to pass through the activated carbon column by driving a pump. Right before the aqueous solution of kasugamycin hydrochloride had become no longer remaining at the surface of the top of the activated carbon column, 120 ml of deionized water were additionally loaded on the top of the carbon column. The aqueous solution was passed at a flow rate of about 6 ml/hour through the activated carbon column.

(2) First step (the hydrolysis step)

As the effluent which flowed from the outlet in the bottom of the activated carbon column, there was obtained an aqueous solution (pH 4) of the preliminarily purified kasugamycin hydrochloride. This aqueous solution was continuously introduced into a column (having an inner diameter of 2.5 cm and a height of 24.5 cm) which was packed with 120 ml of a strongly acidic ion-exchange resin ("Diaion"® SK116, $H^+$-form) and which was placed in an oven heated at 90° C., so that the aqueous solution was passed upwardly through the resin column. At that time, the retention time of the passing solution to reside within the resin column was set at about 7 hours.

In the aqueous solution which was passing through the strongly acidic ion-exchange resin column, the hydrolysis of kasugamycin took place so that DCI was produced. From the outlet of the resin column, the acidic reaction solution containing DCI (pH 1.0) flowed out.

(3) Second step (the step for elimination of basic substances)

The acidic reaction solution as obtained in the above first step was introduced into a column (having an inner diameter of 2.4 cm and a height of 22 cm) as packed with 100 ml of a strongly acidic ion-exchange resin ("Diaion"® C-20, $H^+$-form), so that said reaction solution was passed through said column. The acidic aqueous solution containing DCI flowed out of the resin column.

(4) Third step (the neutralization step)

The DCI-containing acidic aqueous solution as obtained in the above second step was introduced into a column (having an inner diameter of 2.4 cm and a height of 26.5 cm)

as packed with 120 ml of a strongly basic ion exchange resin ("Diaion"® A-113PLUS, OH⁻-form), so that said aqueous solution was passed through the column. From an outlet of the "Diaion"® A-113PLUS column, the neutralized aqueous eluate containing DCI was obtained as the column effluent.

The time required for the preliminary purification step using the activated carbon column as well as the time required for the operations of the above-mentioned first to third steps were totally about 40 hours, including the time needed for washing the resin columns with water.

(5) Fourth step (the step for crystallization of DCI)

After collecting the DCI-containing aqueous solution which flowed from the "Diaion"® A-113PLUS column in the above third step, this resin column was washed with water. The aqueous washing obtained was combined with said aqueous solution of DCI as said column effluent. The content of DCI in the mixed aqueous solution so combined was measured by high-performance liquid chromatography and was found to be 6.8 g (as compared to the theoretical value of 7.1 g) (with a yield of 95% and purity of about 99%). Said mixed solution was concentrated, and ethanol was then added to the resulting concentrated solution to crystallize DCI, so that 6.5 g of crystals of DCI (at a yield of 92% and purity of 100%) were harvested.

EXAMPLE 13

This Example illustrates an example in which preparation of DCI was conducted using an aqueous solution of a crude kasugamycin containing impurities as the starting material in accordance with the process of the fourth aspect of the present invention. The crude kasugamycin employed in this Example was such crude kasugamycin which had been obtained by culturing a kasugamycin-producing microorganism and treating the resulting kasugamycin-containing culture broth through the following steps (A) and (B) of isolating and preliminarily purifying kasugamycin.

(A) Preparation of crude kasugamycin from the culture broth of the kasugamycin-producing microorganism

*Streptomyces kasugaensis*, a kasugamycin-producing microorganism, was cultured by a usual method to prepare a kasugamycin-containing culture broth. The culture broth was filtered to collect 2 liters (hereinafter designated as "l") of the kasugamycin-containing broth filtrate (with a kasugamycin potency of 9.8 mg/ml). This broth filtrate was passed through a column (having an inner diameter of 5 cm and a height of 76.5 cm) which was packed with 1.5 l of a strongly acidic ion-exchange resin ("Diaion"® C-20, H⁺-form), whereby kasugamycin was adsorbed on the resin.

Next, this resin column was washed with 4.5 l of deionized water, followed by elution with 4.5 l of a 2N NaOH aqueous solution. An alkaline aqueous eluate coming from the resin column were collected in fractions, and the alkaline, active fractions containing kasugamycin were harvested. The active fractions were combined and then the resultant combined solution was charged into a column (having an inner diameter of 5 cm and a height of 76.5 cm) which was packed with 1.5 l of a strongly acidic ion-exchange resin ("Diaion"® SK116, H⁺-form), so that the solution was passed through the column at such a flow rate as increased to the maximum. Here, a majority of the kasugamycin present in said combined solution of the active fractions could pass through said resin column without being adsorbed on the "Diaion"® SK116 resin but with the alkaline substances being bound onto the resin. The combined solution of the active fractions containing kasugamycin were neutralized thereby. From the "Diaion"® SK116 column, there was thus collected a neutralized aqueous solution of kasugamycin as the effluent.

The neutralized aqueous solution of kasugamycin was so obtained at a volume of 2,300 ml and was then concentrated by a rotary evaporator, whereby 75 ml of a concentrated aqueous solution containing kasugamycin at a concentration of 200 mg/ml and having a pH of about 7 were obtained. Incidentally, when this concentrated aqueous solution of kasugamycin was evaporated to dryness under reduced pressure, the resulting solid residue was found to consist of 25.0 g of kasugamycin having about 60% purity.

(B) Preliminary purification of the crude kasugamycin

In a manner same as in Example 12, 75 ml of the concentrated aqueous solution of kasugamycin (pH: about 7) as obtained in the step (A) above were introduced into the column of activated carbon as employed in the preliminary purification step of Example 12 and were passed through the carbon column at a flow rate of about 6 ml per hour.

(C) Production and purification of DCI

The aqueous solution of kasugamycin, which had been preliminarily and partially purified by the activated carbon column in the preceding step (B) above but still contained some quantities of impurities, was collected and then continuously introduced into a column which was packed with a strongly acidic ion-exchange resin ("Diaion"® SK116, H⁺-form) and worked as the hydrolyzing reactor same as that employed in the first step of Example 12. Similarly to the first step of Example 12, the temperature of the solution passing through the resin column was raised to 90° C., while the solution being passed with a retention time of about 7 hours. The resulting acidic reaction solution (pH: 1.4) flowed from the column of "Diaion"® SK116, and this solution contained DCI as produced by the hydrolysis of kasugamycin.

The above-mentioned acidic reaction solution was introduced and treated in a column of "Diaion"® C-20 (H⁺-form) similarly to the second step of Example 12. The effluent from this "Diaion"® C-20 column was introduced and treated in a column of "Diaion"® A-113PLUS (OH⁻-form) similarly to the third step of Example 12.

The resulting neutralized aqueous DCI solution was obtained as the effluent from the column of "Diaion"® A-113PLUS" (OH⁻-form) above, and this DCI solution was treated in a manner same as in the fourth step of Example 12, to give 6.7 g of DCI (with a purity of about 99% and at a yield of 93%). This crude but crystalline DCI product was then recrystallized by procedures same as those described before, to afford 6.5 g of colorless crystals of DCI (at a yield of 92% and purity of 100%).

EXAMPLE 14

This Example demonstrates that, even if the step for preliminary purification of crude kasugamycin by the activated carbon column as shown in Example 12 is omitted, but as long as such a kasugamycin which has been purified beforehand to a high purity is used as the starting material, it is feasible to prepare DCI of a high purity at a high yield, when the process of the fourth aspect of the present invention is so performed that the high-purity kasugamycin is directly subjected to the hydrolytic reaction in the same manner as in the first step of Example 12 and the resulting acidic reaction solution is then subjected to the post-treatments same as those conducted in the second to third steps of Example 12.

(A) Preparation of kasugamycin of a high purity

Crystals (18 g) of kasugamycin hydrochloride were dissolved in 700 ml of deionized water, and the resulting aqueous solution was passed through a 600 ml column (having an inner diameter of 5 cm and a height of 30 cm) of a strongly acidic ion-exchange resin ("Diaion"® C-20, H$^+$-form), so that the kasugamycin present in the aqueous solution was made adsorbed on said resin. After washing the resin column with 1.8 l of deionized water, the column was eluted with 2.4 l of 2% aqueous ammonia, and a kasugamycin-containing eluate was collected from the column. Here, the eluate was collected in 100 ml-fractions. The kasugamycin began to be eluted in a little quantity in the fraction No. 10 and was eluted much in the subsequent fractions. The eluate fractions containing kasugamycin were collected and then lyophilized, whereby 15 g of a highly pure kasugamycin (with a purity of 98%) were obtained.

(B) Preparation of DCI from the highly pure kasugamycin and purification of DCI

The highly pure kasugamycin as obtained in the above step (A) was dissolved in deionized water, to prepare about 70 ml of an aqueous solution of kasugamycin which contained kasugamycin at a concentration of about 200 mg/ml but was substantially completely free from the impurities.

The above aqueous solution of kasugamycin was continuously introduced at a temperature of the solution of 90° C. directly into a column which was packed with a strongly acidic ion-exchange resin ("Diaion"® SK116, H$^+$-form), and which resin column was same as that employed in the first step of Example 12. Thereafter, similarly to the first step of Example 12, the aqueous solution of kasugamycin was passed at a reaction temperature of 90° C. and a flow rate of about 6 ml/hour through the resin column, with controlling the retention time of the solution in the column to about 7 hours, whereby the hydrolytic reaction of kasugamycin was effected.

The acidic reaction solution (pH 1.4), which was flown from the "Diaion"® SK116 column, contained DCI so produced.

This acidic reaction solution was then treated in the same manner as in the procedures of the second, third and fourth steps of Example 12, to afford 6.7 g of DCI of a high purity (at a yield of 97% and purity of 100%).

EXAMPLE 15

This Example illustrates preparation of DCI by the process according to the third aspect of the present invention.

(1) First step

Twenty grams of kasugamycin hydrochloride were weighed and placed in an eggplant-shaped flask of 500 ml-capacity, followed by addition of 100 ml of water thereto to prepare an aqueous solution of kasugamycin hydrochloride. This aqueous solution was added with 150 ml of a strongly acidic ion-exchange resin ("Diaion"® SK116, H$^+$-form), followed by through mixing. The whole mixture obtained was heated over an oil bath under an atmospheric pressure at 95° C for 12 hours, so that the hydrolytic reaction of kasugamycin was effected.

The whole reaction mixture so obtained was cooled and then filtered to remove the strongly acidic ion-exchange resin and obtain the acidic reaction solution containing DCI. The resin, which had been filtered off, was washed with 150 ml of water to give the aqueous washing.

(2) Second step (the step for elimination of basic substances)

The aqueous washing and the above acidic reaction solution were combined together. About 250 ml of the resulting acidic reaction solution were charged into a column (having an inner diameter of 2.4 cm and a height of 22 cm) as packed with a strongly acidic ion-exchange resin ("Diaion"® C-20, H$^+$-form, 100 ml), and was passed through the resin column. After the reaction solution had flowed as the effluent from the resin column, the resin column was washed with 100 ml of deionized water. The aqueous washing obtained was combined with the aqueous effluent which was flown out of said resin column, to give about 350 ml of an acidic aqueous solution containing DCI.

(3) Third step (the neutralization step)

The above acidic aqueous solution was loaded on the top of a column (having an inner diameter of 3.0 cm and a height of 21 cm) as packed with a strongly basic ion-exchange resin ("Diaion"® A-113PLUS, OH$^-$-form, 150 ml), and was passed through the resin column. The first 100 ml fraction of the eluate from the column were discarded but the next fractions of about 250 ml of the eluate were collected. Further, the resin column was washed with 150 ml of deionized water. About 150 ml of the aqueous washing obtained was combined with the previously-collected fractions of the eluate from the column, to afford about 400 ml of a neutral aqueous solution containing DCI.

(4) Fourth step (the step for crystallization of DCI)

About 400 ml of the neutral aqueous solution as obtained in the above third step were concentrated to about 40 ml in a rotary evaporator, and the concentrated solution was heated to about 70° C. To the concentrated solution was added under stirring 360 ml of ethanol which had been heated to 70° C. The resulting liquid mixture was left still at room temperature for 12 hours, so that crystallization of DCI was effected. After crystals had deposited, 7.5 g of DCI crystals were harvested by filtration (at a yield of 90% and purity of 100%).

EXAMPLE 16

An aqueous solution of 20 g of kasugamycin hydrochloride in 100 ml of water was charged in a 300 ml glass flask for use in an autoclave. Added to said aqueous solution were 150 ml of particles of a strongly acidic ion-exchange resin ("Diaion"® SK116, H$^+$-form), followed by through mixing. The mixture so obtained was placed in the autoclave while the flask containing said mixture was transferred therein. Under an elevated pressure of 1.2 kg/cm$^2$ (gauge), said mixture was heated at 120° C. for 3 hours so that kasugamycin was hydrolyzed. Subsequent procedures for the treatment of the reaction solution so obtained from the hydrolytic reaction of kasugamycin were conducted similarly to Example 15, whereby 7.8 g of DCI crystals were obtained (at a yield of 94% and purity of 100%).

EXAMPLE 17

A glass-made column (having an inner diameter of 30 mm and a height of 310 mm), which had been packed with 150 ml of a strongly acidic ion-exchange resin ("Diaion"® SK116, H$^+$-form was placed in a heating oven which was controlled at 95° C. An aqueous solution of 20 g of kasugamycin hydrochloride in 100 ml of water was continuously introduced into the resin column, and was passed at a flow rate such that the solution could pass through the resin column in about 12 hours. The kasugamycin was hydrolyzed in the aqueous solution while said aqueous solution was passing through the resin column.

The aqueous effluent which flowed from the resin column was collected, followed by washing the resin column with water. The effluent was combined with the aqueous washing so that 250 ml of a. liquid mixture were obtained. Procedures for the post-treatments of said liquid mixture were conducted as in Example 15, whereby 7.8 g of DCI crystals were obtained (at a yield of 94% and purity of 100%).

The above-described experimental results of Examples 1–17 are summarized in Table 1a to Table 1b, given hereinafter. In addition, in Table 1a to Table 1b there are also shown experimental results of Comparative Example 1-4, which will be described below.

Comparative Example 1

This Example illustrates an experiment in which, pursuant to the method disclosed in U.S. Pat. No. 5,091,596, hydrolysis of kasugamycin was effected with hydrochloric acid, followed by the purification of DCI so produced.

(1) Added to 10.0 g of crystals of kasugamycin hydrochloride (with a purity of 99%) were 31 ml of 5N hydrochloric acid, followed by making the hydrolysis under an atmospheric pressure at 90° C. for 8 hours, and it was found that the yield of DCI contained in the resulting reaction solution was equivalent to 89%. This reaction solution was subjected to silica gel TLC in the same manner as in Example 1, to determine the presence of by-products which were contained in the reaction solution. Spots which indicated the presence of large amount of by-products were observed in the vicinity of Rf=0.58. In addition, spots which indicated the presence of large amounts of by-products other than DCI were also observed near to Rf=0.39 by making the color developments with ninhydrin and iodine vapor.

(2) After the hydrolytic reaction of kasugamycin, the resulting reaction solution was diluted two-fold with distilled water to a liquid volume of about 70 ml. This diluted but still strongly acidic reaction solution was introduced into a column (250 ml, 3×35 cm) containing "Amberlite"® IR410 (OH⁻-form) and was passed through this resin column. The resin column was then washed with 500 ml of distilled water. The hydrogen-ion concentration of the DCI-containing fractions (volume: 440 ml, tinged by a dark yellow color) of the eluate which flowed from the resin column was examined with aid of TB paper. The color tone of the TB paper turned to a dark blue color, thereby indicating that the aqueous solution of the DCI-containing fractions was strongly alkaline.

(3) The above aqueous solution of the DCI-containing fractions was next introduced into a column (250 ml, 3×35 cm) containing a strongly acidic ion-exchange resin ("Amberlite"® IR120B, H⁺-form) and was passed through this resin column. The resin column was thereafter washed with 500 ml of distilled water. The DCI-containing fractions (volume: 500 ml, as a colorless and clear solution) of the eluate which flowed out of said resin column were checked with aid of TB paper. The color tone of the TB paper remained unchanged, thereby indicating a weak acidity of the DCI-containing fractions of the aqueous eluate. Activated carbon (0.76 g) was next added to the DCI-containing fractions of the aqueous eluate, followed by stirring at 5° C. for 2 hours. The resultant whole mixture was filtered through a filter paper to remove the activated carbon and give the filtrate. The activated carbon separated was then washed with deionized water. The filtrate was mixed with the aqueous washing from the activated carbon to afford 520 ml of a liquid mixture. This liquid mixture was concentrated to dryness, to afford 3.9 g of crude crystals of DCI (with a purity of about 92%).

(4) Next, 10 ml of distilled water were added to 3.9 g of the crude DCI crystals obtained as above, followed by heating to about 70° C. The resulting solution was added with 70 ml of ethanol which had been heated to about 70° C., and the mixture so obtained was stirred. The resultant liquid mixture was allowed to stand still at room temperature for about 12 hours so that DCI crystals were made to deposit. The DCI crystals were collected by filtration and then dried, to give 3.4 g of crystals of DCI (at a yield of 82% and purity of 100%). The purity of this DCI product was analyzed by liquid chromatography.

Comparative Example 2

Following the method disclosed in U.S. Pat. No. 5,091,596, the hydrolysis of kasugamycin was effected with 5N hydrochloric acid.

Thus, 22 g of kasugamycin hydrochloride were dissolved in 110 ml of 5N hydrochloric acid. The solution (pH value <0.2) so obtained was subjected to the hydrolytic reaction at 90° C. for 8 hours. The resulting reaction solution was then diluted with 170 ml of water.

The acidity of the aqueous solution so diluted was neutralized and, in order to eliminate the unreacted remaining kasugamycin and the impurities, the diluted solution was charged into a column containing 300 g of a mixture of a strongly acidic ion-exchange resin ("Amberlite"® IR120B, H⁺-form) and a strongly basic ion-exchange resin "Amberlite"® IR410 (OH⁻-form). A neutral effluent flowed out of the mixed resin column and was collected, followed by washing the resin column with water. The aqueous washing and the column effluent were combined together to give 850 ml of a liquid mixture. This liquid mixture was decolorized by treating with 1.7 g of activated carbon for 2 hours at 5° C. Thereafter, the liquid mixture so treated was concentrated to dryness to give 7.6 g of crude powder of DCI (at a yield of 81.5%).

Purification of this crude powder of DCI was then conducted as in Example 1 above, whereby 7.2 g of DCI crystals were obtained (at a yield of 79% and purity of 100%).

Comparative Example 3

The procedures of Comparative Example 2 above were repeated using 0.1N hydrochloric acid instead of 5N hydrochloric acid in the hydrolysis step of kasugamycin. The reaction solution was obtained after the reaction had been conducted at 90° C. for 8 hours. The reaction solution showed a pH value of 1.78. Analysis of said reaction solution by liquid chromatography indicated that no DCI was produced in said reaction solution.

Comparative Example 4

The procedures of Comparative Example 2 above were repeated using 1N hydrochloric acid instead of 5N hydrochloric acid in the hydrolysis step of kasugamycin. The reaction solution obtained from the hydrolysis showed a pH value of 0.87. The yield of DCI formed in said reaction solution was 34.4% (as measured through an analysis by liquid chromatography).

TABLE 1a

| | Hydrolysis step | | | | | Purification step | DCI Crystallization step | | |
|---|---|---|---|---|---|---|---|---|---|
| Example | Kasugamycin (g), (purity, %) | Kind of resin** (amount of resin used, ml) | Reaction temperature (°C.) (reaction time, hr) | Pressure (Gauge) in reaction vessel (kg/cm²) | Reaction procedures | Yield of DCI in reaction solution (%)*** | Amount of resin needed (ml)**** | Amount of solution to be concentrated (ml) | Yield of DCI crystals (g) (purity, %) | Yield of crystalline DCI (%) |
| 1 | 15.5 (97) | A (100) | 95 (12) | 0 | BR, with stirring | 98 | 170 | 300 | 5.8 (100) | 94 |
| 2 | 15.0* (98) | A (100) | 95 (12) | 0 | BR, with stirring | 98 | 170 | 300 | 6.6 (100) | 94 |
| 3 | 10.0 (99) | A (50) | 95 (24) | 0 | BR, without stirring | 96 | 110 | 200 | 3.75 (100) | 91 |
| 4 | 10.0 (99) | A (100) | 95 (24) | 0 | BR, without stirring | 99 | 110 | 200 | 3.89 (100) | 95 |
| 5 | 10.0 (99) | A (50) | 95 (48) | 0 | BR, without stirring | 99 | 110 | 200 | 3.88 (100) | 95 |
| 6 | 10.0 (99) | A (50) | 100 (24) | 0 | BR, without stirring | 98 | 110 | 200 | 3.84 (100) | 94 |
| 7 | 10.0 (99) | A (50) | 110 (6) | 0.5 | BR, without stirring | 96 | 110 | 200 | 3.77 (100) | 92 |
| 8 | 10.0 (99) | A (50) | 120 (1) | 1.2 | BR, without stirring | 96 | 110 | 200 | 3.79 (100) | 92 |
| 9 | 10.0 (99) | A (50) | 120 (3) | 1.2 | BR, without stirring | 98 | 110 | 200 | 3.85 (100) | 94 |
| 10 | 10.0 (99) | A (50) | 120 (6) | 1.2 | BR, without stirring | 99 | 110 | 200 | 3.91 (100) | 95 |

TABLE 1b

| | Hydrolysis step | | | | | Purification step | DCI Crystallization step | | |
|---|---|---|---|---|---|---|---|---|---|
| Example | Kasugamycin (g), (purity, %) | Kind of resin** (amount of resin used, ml) | Reaction temperature (°C.) (reaction time, hr) | Pressure (Gauge) in reaction vessel (kg/cm²) | Reaction procedures | Yield of DCI in reaction solution (%)*** | Amount of resin needed (ml)**** | Amount of solution to be concentrated (ml) | Yield of DCI crystals (g) (purity, %) | Yield of crystalline DCI (%) |
| 11 | 10.0 (99) | B (50) | 120 (3) | 1.2 | BR, without stirring | 97 | 110 | 200 | 3.78 (100) | 92 |
| 12 | 24.0 (71) | A (120) | 90 (retention time for 7 hrs.) | ---- | RC | 100 | 220 | 200 | 6.5 (100) | 92 |
| 13 | 25.0* (60) | A (120) | 90 (retention time for 7 hrs.) | ---- | RC | 100 | 220 | 180 | 6.5 (100) | 92 |
| 14 | 15.0* (98) | A (120) | 90 (retention time for 7 hrs.) | ---- | RC | 100 | 220 | 180 | 6.7 (100) | 96 |
| 15 | 20.0 (100) | A (150) | 95 (12) | 0 | BR, without stirring | 94 | 250 | 400 | 7.5 (100) | 90 |
| 16 | 20.0 (100) | A (150) | 120 (3) | 1.2 | BR, without stirring | 99 | 250 | 400 | 7.8 (100) | 94 |
| 17 | 20.0 (100) | A (150) | 95 | ---- | RC | 99 | 250 | 400 | 7.8 (100) | 94 |
| Comparative Example-1 | 10.0 (99) | (5N—HCl, 31 ml) | 90 (8) | 0 | BR, without stirring | 89 | 500 | 520 | 3.4 (100) | 82 |
| Comparative Example-2 | 22.0 (100) | (5N—HCl, 110 ml) | 90 (8) | 0 | BR, without stirring | 89 | (300 g) | 850 | 7.2 (100) | 79 |
| Comparative Example-3 | 22.0 (100) | (0.1N—HCl, 110 ml) | 90 (8) | 0 | BR, without stirring | 0 | ---- | ---- | ---- | ---- |
| Comparative Example-4 | 22.0 (100) | (1N—HCl, 110 ml) | 90 (8) | 0 | BR, without stirring | 34 | ---- | ---- | ---- | ---- |

In Table 1a and Table 1b shown above, (i) *: The mark (*) indicates use of kasugamycin, while the absence of the mark (*) indicates use of kasugamycin hydrochloride in all cases.

(ii) **: Under the column for the "kind of resin", "A" stands for "Diaion" SK116 and "B" stands for "Duolite" CC204F.

(iii) Under the column for the "reaction procedures", "BR" indicates that the hydrolysis was conducted in a reactor which was operable batchwise, and "RC" designates that the hydrolysis was conducted by introducing an aqueous solution of the starting material into a resin column and then passing the solution through the resin column.

(iv) ***: Under the column for the "yield of DCI in reaction solution", the yield of DCI indicates the values of the yield as measured through an analysis by high-performance liquid chromatography.

(v) ****: by the term "amount of resins needed" is meant the total of the amounts of the strongly acidic ion-exchange resin and the strongly basic ion-exchange resin, which were needed for the purification of DCI.

(vi) With respect to the Comparative Examples 1 and 2, the term "amount of resins needed" under the column for "Purification step" indicates the total of the amounts of the strongly acidic ion-exchange resin and the strongly basic ion-exchange resin, both, needed for the treatments of the reaction solution which was obtained from the step for the hydrolysis of kasugamycin with hydrochloric acid according to the prior art method of the aforesaid U.S. patent.

As a process for the preparation of DCI to be conducted on a commercial scale, the processes according to the present invention are very much advantageous in the undermentioned points, as compared with the above prior art method comprising hydrolysis of kasugamycin with an aqueous solution of a strong acid.

(1) According to the processes of the present invention, DCI of a high purity can be harvested at a high yield by simple procedures under mild reaction conditions but without involving side-reactions.

Described specifically, the processes according to the present invention comprise conducting the hydrolysis of kasugamycin with using a strongly acidic ion-exchange resin but without relying on the prior art method which makes use of a liquid acid. The use of the strongly acidic ion-exchange resin makes it possible to increase the yield of DCI present in the reaction solution obtained from the hydrolysis, to 90% or higher of the theoretical yield of DCI. This is extremely advantageous, as compared with the fact that the yield of DCI in the hydrolytic reaction solution obtained according to the prior art method is normally at the level of 80%. According to the processes of the present invention, the DCI yield of a high level which can be attained in the hydrolysis step continues to be maintained until to the final stage of the recovery of DCI, consequently with ensuring that DCI of 100% purity is always obtained at a yield significantly higher than 90%. Moreover, the processes of the present invention are to perform the hydrolysis of kasugamycin with using a strongly acidic ion-exchange resin, whereby it is made possible to save and substantially reduce the amounts of resins, which are required in the purification steps of DCI done after the hydrolysis step, to a volume as little as about 1/5 to 2/5-folds less than the volume of the resins which was required in the prior art method. Further, the amount of the aqueous solution of DCI, which must be concentrated for effecting the crystallization of DCI, can be as small as about 2/5 to 3/5-folds in volume less than that required in the prior art method, and hence a smaller device for the concentrating step and a shorter time for the concentrating step are needed only.

(2) When the hydrolytic reaction of kasugamycin is carried out at elevated temperature and pressure which have become usable by the present invention, the reaction time can time can be shortened to about 1/4-folds compared with such procedure where the reaction is conducted under an atmospheric pressure.

(3) The strongly acidic or basic ion-exchange resin as employed in the hydrolysis step or the subsequent steps of the processes of the present invention can be re-used by its regeneration with an aqueous solution of an alkali or an acid.

(4) The amount of the acid or alkali which is to be used upon the regeneration of the strongly acidic or basic ion-exchange resin as employed in the hydroltic reaction or the subsequent steps can be reduced to about one-third-folds less than the amount of the acid or alkali which was used in the prior art method of the U.S. patent referred to above. Further, the devices required for the regenerating treatments of the resins can be reduced in size, and the labor needed for the treatment of the resultant waste-water and the like can also be reduced considerably.

INDUSTRIAL UTILIZABILITY

As described above, the processes according to the present invention are able to achieve the preparation of D-chiro-inositol by conducting the hydrolysis of kasugamycin in a facile way under mild reaction conditions and at a high rate of the reaction, with utilizing a strongly acidic ion-exchange resin ($H^+$-form). The processes according to the present invention render it feasible to prepare D-chiro-inositol of a high purity at a high yield, and can be commercially practised with many advantages.

We claim:

1. A process for the preparation of D-chiro-inositol comprising mixing an aqueous solution of kasugamycin or a salt thereof with particles of a strongly acidic ion-exchange resin of the $H^+$-form, heating the resulting mixture under an atmospheric pressure or an elevated pressure to effect hydrolysis of kasugamycin, separating the resulting acidic reaction solution containing D-chiro-inositol so formed, from the strongly acidic ion-exchange resin, thereby to obtain the acidic reaction solution containing D-chiro-inositol, and then recovering D-chiro-inositol from said acidic reaction solution.

2. A process for the preparation of D-chiro-inositol comprising continuously introducing an aqueous solution of kasugamycin or a salt thereof into a column packed with a strongly acidic ion-exchange resin of the $H^+$-form, heating the aqueous solution of kasugamycin and the resin within said column under an atmospheric pressure or an elevated pressure to effect hydrolysis of kasugamycin, allowing the resulting acidic reaction solution containing D-chiro-inositol so formed, to flow out of the resin column, and recovering D-chiro-inositol from said acidic reaction solution.

3. A process for the preparation of D-chiro-inositol comprising conducting successively the following first to fourth steps:

in a first step, mixing an aqueous solution of kasugamycin or a salt thereof with particles of a strongly acidic ion-exchange resin of the $H^+$-form, heating the resulting mixture under an atmospheric pressure or an elevated pressure to effect hydrolysis of kasugamycin, separating the resulting acidic reaction solution containing D-chiro-inositol so formed, from the strongly acidic ion-exchange resin, thereby to obtain the acidic reaction solution containing D-chiro-inositol, in a second step, passing said acidic reaction solution so obtained in the first step, through a column packed with a strongly acidic ion-exchange resin of the $H^+$-form, to eliminate the basic impurities contained in said reaction solution and, removing any unreacted kasugamycin, whereby an acidic aqueous solution containing D-chiro-inositol is obtained, in a third step, passing said acidic aqueous solution so obtained in the second step, through a column packed with a strongly basic ion-exchange resin of the $OH^-$-form, thereby to obtain a neutralized aqueous eluate containing D-chiro-inositol, and in a fourth step, concentrating said eluate so obtained in the third step, to deposit D-chiro-inositol of a high purity from the resulting concentrated solution.

4. A process for the preparation of D-chiro-inositol comprising conducting the following first to fourth steps:

in a first step, continuously introducing an aqueous solution of kasugamycin or a salt thereof into a column packed with a strongly acidic ion-exchange resin of the $H^+$-form, heating under an atmospheric pressure or an elevated pressure the aqueous solution of kasugamycin and the resin within the column to effect hydrolysis of the kasugamycin, and allowing the resulting acidic reaction solution containing d-chiro-inositol so formed, to flow out of the resin column, thereby to obtain the acidic reaction solution containing D-chiro-inositol, in a second step, passing the acidic reaction solution so obtained in the first step, through a column packed with a strongly acidic ion-exchange resin of the $H^+$-form, to eliminate the basic impurities contained in said reaction solution and, removing any unreacted kasugamycin, whereby an acidic aqueous solution containing D-chiro-inositol is obtained, in a third step, passing said acidic aqueous solution so obtained in the second step, through a column packed with a strongly basic ion-exchange resin of the $OH^-$-form, thereby to obtain a neutralized aqueous eluate containing D-chiro-inositol, and in a fourth step, concentrating said eluate so obtained in the third step, to deposit D-chiro-inositol of a high purity to deposit from the resulting concentrated solution.

* * * * *